United States Patent [19]

Pick et al.

[11] Patent Number: 5,462,959
[45] Date of Patent: Oct. 31, 1995

[54] 4-ARYL-IMIDAZOLE DERIVATIVES

[75] Inventors: John H. Pick; Robert T. Logan, both of Lanarkshire, Scotland

[73] Assignee: Akzo N.V., Arnhem, Netherlands

[21] Appl. No.: 136,530

[22] Filed: Oct. 14, 1993

Related U.S. Application Data

[62] Division of Ser. No. 857,526, Mar. 19, 1992, Pat. No. 5,254,575.

[30] Foreign Application Priority Data

Mar. 25, 1991 [EP] European Pat. Off. ............ 91302573

[51] Int. Cl.$^6$ .................... C07D 233/90; A01K 31/415
[52] U.S. Cl. ......................... 514/400; 548/336.1
[58] Field of Search ................ 548/336.1, 333.5; 514/400

[56] References Cited

U.S. PATENT DOCUMENTS 5,023,336  6/1991  Shigehara ........................ 548/110

FOREIGN PATENT DOCUMENTS 822030   3/1975   Belgium .
0199968  11/1986  European Pat. Off. .
2261756  9/1975   France .

OTHER PUBLICATIONS

Kosary, J., "Preparation of Carboxylic Acid Amides From Less Reactive Esters", Chemical Abstracts, vol. 94, No. 7, p. 573, Abstract No. 47247, Feb. 16, 1981, USA.

Primary Examiner—Robert Gerstl
Attorney, Agent, or Firm—Mary E. Gormley; William M. Blackstone

[57] ABSTRACT

The invention concerns a 4-aryl-imidazole derivative having the formula I

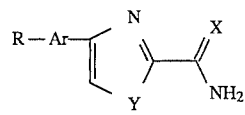

wherein
X is O or NOH,
Y is $NR_3$,
Ar is a group selected from phenyl, naphthyl, tetrahydronaphthyl, and biphenyl,
R is one to four substituents independently selected from hydrogen, hydroxy, lower alkyl, lower alkoxy, lower thioalkyl, cycloalkyl, halogen, $CF_3$, $NO_2$, and O—ALK—$NR_1R_2$, in which ALK is a saturated aliphatic hydrocarbon group having 2–6 carbon atoms, and $R_1$ and $R_2$ are independently hydrogen or lower alkyl, or form, together with the nitrogen atom to which they are bonded, a heterocyclic ring, and
$R_3$ is hydrogen or a lower alkyl; or a pharmaceutically acceptable salt thereof, with the proviso that 4-(4-chlorophenyl)-thiazole-2-carboxamide is excluded. The compounds according to the invention increase the sensitivity of cardiac myofibrils to calcium and possess phosphodiesterase inhibitory activity and bronchodilator activity, and are useful for the treatment of patients suffering from heart failure and asthma.

5 Claims, No Drawings

4-ARYL-IMIDAZOLE DERIVATIVES

This is a division of application Ser. No. 07/857,526 filed Mar. 25, 1992, now U.S. Pat. No. 5,254,575.

The invention concerns 4-aryl-thiazole or imidazole derivatives, a process for the preparation and a use thereof, and a pharmaceutical composition containing the same.

Related derivatives are known. The synthesis of 4-(4-chlorophenyl)-thiazole-2-carboxamide has been described by J. Kosary, Magy. Kem. Foly, 1980, 86(6), 282 (Chem. Abstr., 1981, (94), 47247s). No pharmacological activity was, however, disclosed. In Belgian patent application BE 822 030 4-phenyl-thiazole-2-carboxamide is disclosed as a drug to inhibit gastric secretion, to treat ulcers, and to combat inflammatory processes.

The compounds according to the invention increase the sensitivity of cardiac myofibrils to calcium. An increase in calcium sensitivity improves cardiac function in heart failure patients in an energetically favourable manner, without the danger of producing concurrent calcium overload in the myocardial cell. The compounds also possess phosphodiesterase inhibitory activity and bronchodilator activity, and are useful for the treatment of patients suffering from asthma. This invention, therefore, also provides pharmaceutical compositions containing one of more of the compounds of the invention, the use thereof for the preparation of a medicament and a method for the treatment of heart failure and asthma in mammals.

The invention concerns a 4-aryl-thiazole or imidazole derivative having the formula I

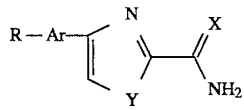

wherein

X is O or NOH,

Y is S or $NR_3$,

Ar is a group selected from phenyl, naphthyl, tetrahydronaphthyl, and biphenyl,

R is one to four substituents independently selected from hydrogen, hydroxy, lower alkyl, lower alkoxy, lower thioalkyl, cycloalkyl, halogen, $CF_3$, $NO_2$, and O—ALK—$NR_1R_2$, in which ALK is a saturated aliphatic hydrocarbon group having 2–6 carbon atoms, and $R_1$ and $R_2$ are independently hydrogen or lower alkyl, or form, together with the nitrogen atom to which they are bonded, a heterocyclic ring, and $R_3$ is hydrogen or a lower alkyl; or a pharmaceutically acceptable salt thereof, with the proviso that 4-(4-chlorophenyl)-thiazole-2-carboxamide is excluded.

Preferred compounds according to the invention are 4-phenylthiazole and imidazole derivatives, wherein X is NOH, Y is S or NH, and Ar is phenyl, and more preferably compounds wherein X is NOH, Y is S or NH, Ar is phenyl, and at least one of the substituents R is methyl, methoxy, or chlorine, or pharmaceutically acceptable salts thereof.

Specifically useful compounds are 4-(3-chloro- 4,5-dimethoxyphenyl)-N-hydroxy-thiazole-2-carboximidamide, 4(3,4-dichlorophenyl)-N-hydroxy-thiazole-2-carboximidamide, N-hydroxy-4-(4,5-dimethoxyphenyl)-thiazole-2carboximidamide, and N-Hydroxy-4-(3,4-dimethylphenyl)-1H-imidazole-2-carboximidamide, or pharmaceutically acceptable salts thereof.

Derivatives where Y is $NR_3$ (imidazoles) show in general better water solubility than derivatives where Y is S (thiazoles), making these compounds particularly suitable for use in injection preparations. In preferred imidazoles, $R_3$ is hydrogen.

The term lower alkyl means a branched or unbranched alkyl group having preferably 1–6 carbon atoms, such as methyl, ethyl, propyl, isopropyl, butyl, tert-butyl, pentyl, hexyl and the like. Preferred are alkyl groups having 1–4 carbon atoms, and most preferred is the methyl group.

The alkyl moiety which is present in the lower alkoxy and lower thioalkyl groups has the same meaning as previously defined for lower alkyl.

The term cycloalkyl means a cycloalkyl group having 5–7 carbon atoms, such as cyclopentyl or cyclohexyl.

The term halogen used in the definition of formula I means fluorine, chlorine, bromine or iodine. Chlorine is the preferred halogen.

The term ALK means a saturated branched or unbranched aliphatic hydrocarbon group having 2–6 carbon atoms. Examples are 1,2-ethanediyl, 1,3-propanediyl, 1,4-butanediyl, 1-methyl-1,2-ethanediyl and 2,4-dimethyl1,4-butanediyl.

Preferred ALK groups are unbranched hydrocarbon groups with 2–4 carbon atoms. Most preferred is the 1,2-ethanediyl group.

The ring which may be formed by $R_1$ and $R_2$ and the nitrogen atom to which they are bonded, is a 5- or 6-membered ring, which may have a second hetero atom and may be substituted with lower alkyl. Examples are piperidinyl, morpholinyl, piperazinyl, N-methylpiperazinyl, and pyrrolidinyl.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, or ascorbic acid.

The 4-aryl-thiazole or imidazole derivative according to this invention, can be prepared by methods known in the art. A suitable process for the preparation of these compounds is characterized in that a 4-aryl-thiazole or imidazole derivative having formula II

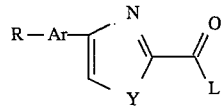

in which R, Ar, and Y have the previously given meanings, and L is a leaving group, like hydroxy, halogen (preferably chlorine or bromine), or alkoxy (preferably methoxy), is condensed with ammonia, to give the derivative of formula I wherein X=O, after which the derivative obtained may optionally be converted into the derivative of formula I wherein X=NOH, and/or converted into a pharmaceutically acceptable salt.

4-aryl-thiazole or imidazole derivatives having formula II can be prepared by customary synthetic methods, for instance by condensation of aminothioacetate esters and suitable aromatic ketones, as is illustrated more specifically in the examples.

The conversion of the carboxamide derivatives of formula I (X=O) into the N-hydroxy-carboximidamide derivatives of formula I (X=NOH), is performed through a nitrile having formula III

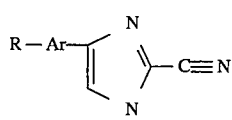

in which R, Ar, and Y have the previously given meanings. The nitrile derivatives of formula III may also be prepared from other starting materials than the carboxamides of formula I, for example from the corresponding aldehydes, which can be converted into the nitriles via an oxime, by methods well known to the skilled organic chemist.

It is possible to convert the products obtained by one of the previously mentioned procedures into another product according to the invention. Using generally known methods it is, for instance, possible to convert aromatic substituents into other aromatic substituents. Alkoxy substituents may be treated with strong acids, such as $BBr_3$, to give the hydroxy substituent. Hydroxy substituted compounds may be condensed with lower alcohols in acidic medium to give alkoxy derivatives, with lower thioalcohols to give alkylthio derivatives, or with suitable aminoalcohols ($R_1R_2N$—ALK—OH) or aminoalkylhalides ($R_1R_2N$—ALK-halide) to give compounds of the invention having an $R_1R_2N$—ALK—O substituent. Compounds wherein $R_1$ and/or $R_2$ is hydrogen may be alkylated, e.g. by a Leuckart-Wallach reaction, to afford compounds wherein $R_1$ and/or $R_2$ is alkyl.

The compounds of the invention may be administered enterally or parenterally, and for humans preferably in a daily dosage of 0.001–10 mg per kg body weight. Mixed with pharmaceutically suitable auxiliaries, the compounds may be compressed into solid dosage units, such as pills, tablets, or be processed into capsules, suppositories, or a nebuliser. By means of pharmaceutically suitable liquids the compounds can also be applied as an injection preparation in the form of a solution, suspension, emulsion, or as a spray, e.g. a nasal spray.

Also 4-(4-chlorophenyl)-thiazole-2-carboxamide, the synthesis of which has been described by J. Kosary, Magy. Kem. Foly, 1980, 86(6), 282 (Chem. Abstr., 1981, (94), 47247s), can be mixed with pharmaceutically suitable auxiliaries, and be used in therapy or to prepare a medicament to treat patients suffering from heart failure or asthma.

The invention is further illustrated by the following examples.

EXAMPLE 1

4-(3-Chloro-4,5-dimethoxyphenyl)-thiazole-2-carboxamide a) 1-(3-Chloro-4,5-dimethoxyphenyl)-ethanone (31.6 g) was dissolved in chloroform (140 ml) and the solution was stirred at room temperature and treated dropwise with a solution of bromine (7.9 ml) in chloroform (60 ml). After a further 45 min the mixture was neutralised with aqueous potassium bicarbonate solution. The organic layer was separated and washed with sodium chloride solution, dried over sodium sulphate, then filtered and evaporated to dryness. The resultant oil (42.8 g) was crystallized from ether-hexane to give 2-bromo-1-(3-chloro-4,5-dimethoxyphenyl)-ethanone (32.0 g), m.p. 76.5°–78° C.

b) To a solution of ethyl aminothioxoacetate (16.2 g) in ethanol (80 ml), stirred under nitrogen at reflux, was added dropwise over 10 min, a hot solution of 2-bromo-1-(3-chloro-4,5-dimethoxyphenyl)-ethanone (31.9 g) in ethanol (180 ml). The mixture was heated at reflux for 4 h, then cooled to room temperature. The precipitated solid was collected by filtration and dried under vacuum at 60° C. Recrystallisation from ethanol gave ethyl 4-(3-chloro-4,5-dimethoxyphenyl)-thiazole-2-carboxylate as a white solid (21.9 g), m.p. 92°–94° C.

c) A solution of ethyl 4-(3-chloro-4,5-dimethoxyphenyl)-thiazole-2-carboxylate (21.8 g) in 1,2-ethanediol (150 ml) at 120° C. was treated with ammonia gas for 25 min. The mixture was cooled in an ice-bath and the resultant suspension was filtered, washed with methanol, and dried at 60° C. under vacuum to give 4-(3-chloro-4,5-dimethoxyphenyl)-thiazole-2-carboxamide (18.7 g), m.p. 178°–180° C.

EXAMPLE 2

In an analogous manner, as described in Example 1, were prepared:

4-(4-Methoxyphenyl)-thiazole-2-carboxamide. m.p. 223°–225° C.

4-(2-Chloro-3,4-dimethoxyphenyl)-thiazole-2-carboxamide. m.p. 201°–203° C.

4-(3-Chloro-4-ethoxy-5-methoxyphenyl)-thiazole-2-carboxamide. m.p. 186°–188° C.

4-(4-Hydroxy-3-methoxyphenyl)-thiazole-2-carboxamide. m.p. 137°–142° C.

4-(3-Methoxy-4-methylthiophenyl)-thiazole-2-carboxamide. m.p. 200°–202° C.

4-(3-Chloro-5-methoxy-4-methylthiophenyl)-thiazole-2-carboxamide. m.p. 201°–203° C.

4-(3,4-Dimethoxyphenyl)-thiazole-2-carboxamide. m.p. 190°–191° C.

4-(3-Chloro-4-hydroxy-5-methoxyphenyl)-thiazole-2-carboxamide. m.p. 234°–236° C.

4-(3-Chlorophenyl)-thiazole-2-carboxamide. m.p. 155°–156° C.

4-(2-Chlorophenyl)-thiazole-2-carboxamide. m.p. 125°–127° C.

4-Phenyl-thiazole-2-carboxamide. m.p. 144°–145° C.

4-(3-Methylthiophenyl)-thiazole-2-carboxamide. m.p. 136°–138° C.

4-(3-Nitrophenyl)-thiazole-2-carboxamide. m.p. 247°–248° C.

4-(2-Fluorophenyl)-thiazole-2-carboxamide. m.p. 155°–157° C.

4-(3-Fluorophenyl)-thiazole-2-carboxamide. m.p. 175°–178° C.

4-(3-Bromophenyl)-thiazole-2-carboxamide. m.p. 157°–158° C.

4-[3-(Trifluoromethyl)phenyl]-thiazole-2-carboxamide. m.p. 155°–158° C.

4-(4-Fluorophenyl)-thiazole-2-carboxamide. m.p. 165°–170° C.

4-(4-Bromophenyl)-thiazole-2-carboxamide. m.p. 206°–207° C.

4-[4-(Trifluoromethyl)phenyl]-thiazole-2-carboxamide. m.p. 195°–197° C.

4-(2,3-Dichlorophenyl)-thiazole-2-carboxamide. m.p. 215°–217° C.

4-(3,4-Dichlorophenyl)-thiazole-2-carboxamide. m.p. 215° C.

4-(3,5-Dichlorophenyl)-thiazole-2-carboxamide. m.p. 167°–170° C.

4-(2,5-Dichlorophenyl)-thiazole-2-carboxamide. m.p. 223°–224° C.

4-(3-Methylphenyl)-thiazole-2-carboxamide. m.p. 118°–120° C.

4-(4-Methylphenyl)-thiazole-2-carboxamide. m.p. 205°–206° C.

4-(3,4-Dimethylphenyl)-thiazole-2-carboxamide. m.p. 172°–174° C.

4-(2-Naphthalenyl)-thiazole-2-carboxamide. m.p. 178°–180° C.

4-(5,6,7,8-Tetrahydro-2-naphthalenyl)-thiazole-2-carboxamide. m.p. 159°–162° C.

4-(1,1'-Biphenyl-3-yl)-thiazole-2-carboxamide. m.p. 139°–142° C.

4-Cyclohexylphenyl-thiazole-2-carboxamide.

EXAMPLE 3

4-(3-Chloro-4,5-dimethoxyphenyl)-N-hydroxy-thiazole-2-carboximidamide a) A solution of 4-(3-chloro-4,5-dimethoxyphenyl)-thiazole-2-carboxamide (1.58 g) (Example 1c) in pyridine (9 ml) was cooled to 0° C. and treated with trifluoroacetic anhydride (4 ml) whilst maintaining the internal temperature below 10° C. The mixture was stirred at room temperature for 10 min, then cooled and treated dropwise with water (45 ml) whilst maintaining the internal temperature below 30° C. The precipitated solid was collected by filtration and dried under vacuum at 60° C. Recrystallisation from dichloromethane-ether afforded 4-(3-chloro-4,5-dimethoxyphenyl)-thiazole-2-carbonitrile (1.25 g), m.p. 147°–149° C.

b) Sodium metal (3.9 g) was cut into small pieces and added to methanol (200 ml) stirred under an atmosphere of nitrogen. When all the sodium had dissolved, the hot solution was treated with a warm solution of hydroxylamine hydrochloride (11.6 g) in methanol (200 ml). After 15 min the white suspension of sodium chloride was filtered and the filtrate was added to 4-(3-chloro-4,5-dimethoxyphenyl)-thiazole-2-carbonitrile (15.4 g). A solution was obtained, followed, after 10 min, by precipitation of a colourless solid. After a further 1.5 h the reaction mixture was concentrated to low volume by evaporation, cooled and diluted with water (700 ml). The solid was filtered, dried at 60° C. under vacuum and recrystallised from methanol-water to afford 4-(3-chloro-4,5-dimethoxyphenyl)-N-hydroxy-thiazole-2-carboximidamide (15.3 g), m.p. 169°–170° C.

EXAMPLE 4

In an analogous manner, as described in Example 3, were prepared:

N-Hydroxy-4-phenyl-thiazole-2-carboximidamide. m.p. 145°–146° C.

N-Hydroxy-4-(4-methoxyphenyl)-thiazole-2-carboximidamide. m.p. 192°–194° C.

N-Hydroxy-4-(4-hydroxyphenyl)-thiazole-2-carboximidamide. m.p. 195°–197° C.

N-Hydroxy-4-(3,4-dimethoxyphenyl)-thiazole-2-carboximidamide. m.p. 192°–202° C.

4-(2-Chloro-3,4-dimethoxyphenyl)-N-hydroxy-thiazole-2-carboximidamide. m.p. 180°–183° C.

4-(3-Chloro-4-ethoxy-5-methoxyphenyl)-N-hydroxy-thiazole-2-carboximidamide. m.p. 177°–179° C.

N-Hydroxy-4-(4-hydroxy-3-methoxyphenyl)-thiazole-2-carboximidamide. m.p. 188°–191° C.

N-Hydroxy-4-(3-methoxy-4-methylthiophenyl)-thiazole-2-carboximidamide. m.p. 215°–219° C.

4-(3-Chloro-5-methoxy-4-methylthiophenyl)-N-hydroxy-thiazole-2-carboximidamide. m.p. 200°–202° C.

4-(3-Chlorophenyl)-N-hydroxy-thiazole-2-carboximidamide. m.p. 189°–191° C.

4-(4-Chlorophenyl)-N-hydroxy-thiazole-2-carboximidamide. m.p. 205°–207° C.

4-(2-Chlorophenyl)-N-hydroxy-thiazole-2-carboximidamide. m.p. 176°–178° C.

4-(3-Chloro-4-hydroxy-5-methoxyphenyl)-N-hydroxy-thiazole-2-carboximidamide. m.p. 207°–211° C.

N-Hydroxy-4-[3-(methylthio)phenyl]-thiazole-2-carboximidamide. m.p. 165°–166° C.

N-Hydroxy-4-(3-nitrophenyl)-thiazole-2-carboximidamide. m.p. 227°–230° C.

4-(2-Fluorophenyl)-N-hydroxy-thiazole-2-carboximidamide. m.p. 168°–169° C.

4-(3-Fluorophenyl)-N-hydroxy-thiazole-2-carboximidamide. m.p. 179°–180° C.

4-(4-Fluorophenyl)-N-hydroxy-thiazole-2-carboximidamide. m.p. 171°–176° C.

4-(3-Bromophenyl)-N-hydroxy-thiazole-2-carboximidamide. m.p. 206°–207° C.

4-(4-Chlorophenyl)-N-hydroxy-thiazole-2-carboximidamide. m.p. 205°–207° C.

4-(4-Bromophenyl)-N-hydroxy-thiazole-2-carboximidamide. m.p. 215°–218° C.

N-Hydroxy-4-[3-(trifluoromethyl)phenyl]-thiazole-2-carboximidamide. m.p. 186°–187° C.

N-Hydroxy-4-[4-(trifluoromethyl)phenyl]-thiazole-2-carboximidamide. m.p. 224°–228° C.

4-(2,3-Dichlorophenyl)-N-hydroxy-thiazole-2-carboximidamide. m.p. 190°–191° C.

4-(3,4-Dichlorophenyl)-N-hydroxy-thiazole-2-carboximidamide. m.p. 224°–226° C.

4-(3,5-Dichlorophenyl)-N-hydroxy-thiazole-2-carboximidamide. m.p. 223°–225° C.

4-(2,5-Dichlorophenyl)-N-hydroxy-thiazole-2-carboximidamide. m.p. 189°–190° C.

N-Hydroxy-4-(3-methylphenyl)-thiazole-2-carboximidamide. m.p. 190°–192° C.

N-Hydroxy-4-(4-methylphenyl)-thiazole-2-carboximidamide. m.p. 196°–200° C.

N-Hydroxy-4-(3,4-dimethylphenyl)-thiazole-2-carboximidamide. m.p. 206°–210° C.

N-Hydroxy-4-(2-naphthalenyl)-thiazole-2-carboximidamide. m.p. 202°–204° C.

N-Hydroxy-4-(5,6,7,8-tetrahydro-2-naphthalenyl)-thiazole-2-carboximidamide. m.p. 173°–176° C.

4-(1,1'-Biphenyl-3-yl)-N-hydroxy-thiazole-2-carboximidamide. m.p. 187°–189° C.

4-Cyclohexylphenyl-N-hydroxy-thiazole-2-carboximidamide.

EXAMPLE 5

4-(4-Hydroxyphenyl)-thiazole-2-carboxamide.

Boron tribromide (3.7 ml) was added dropwise under nitrogen to a suspension of 4-(4-methoxyphenyl)-thiazole-2-carboxamide (3 g) in dichloromethane (45 ml). The mixture was stirred at room temperature for 2 h, then under reflux for 2 h and then cooled, after which water (60 ml) was added cautiously. The precipitate was filtered and the collected solid was dried under vacuum at 50° C., and recrystallised from methanol to give 4-(4-hydroxyphenyl)-thiazole-2-carboxamide (2.03 g), m.p. 223°–227° C.

EXAMPLE 6

4-[4-[2-(Piperidin-1-yl)ethyloxy]phenyl]-thiazole-2-carboxamide and N-hydroxy-4-[4-[2-(piperidin-1-yl)ethyloxy]phenyl]-thiazole-2-carboximidamide a) A mixture of 4-(4-methoxyphenyl)-thiazole-2-carbonitrile (14.9 g) and pyridine hydrochloride (44.7 g) was heated at 225° C. for 1 h, then cooled and added to water (300 ml). The suspension was filtered and dried under vacuum at 50° C., to give a solid which was dissolved in methanol, treated with charcoal, filtered and recrystallised from methanol-water to give 4-(4-hydroxyphenyl)-thiazole-2-carbonitrile (9.2 g); m.p. 186°–197° C.

b) A suspension of 4-(4-hydroxyphenyl)-thiazole-2-carbonitrile (7 g), crushed potassium carbonate (13.1 g) and 1-(2-chloroethyl)piperidine hydrochloride (7.78 g) in dry dimethylformamide (60 ml) was stirred at room temperature for 28 h, and then added to water (400 ml). The precipitated solid was filtered, and then partitioned between dichloromethane and water. The organic layer was dried over sodium sulphate, filtered, and evaporated to dryness to give 4-[4-[ 2-(piperidin-1-yl)ethyloxy]phenyl]-thiazole-2-carbonitrile (10.1 g), m.p. 85°–86° C.

c) 4-[4-[2-(piperidin-1-yl)ethyloxy]phenyl]-thiazole-2-carbonitrile was hydrolysed by boiling with 35% aqueous sodium hydroxide or with 60% sulphuric acid for 6 h and converted into its hydrochloride salt to obtain 4-[4-[2-(piperidin-1-yl)ethyloxy]phenyl]-thiazole-2-carboxamide hydrochloride, m.p. 208°–210° C., or according to the method described in Example 3b converted into N-hydroxy-4-[4-[2-(piperidin-1-yl)ethyloxy]phenyl]-thiazole-2-carboximidamide hydrochloride (1:1) salt, m.p. >260° C.

EXAMPLE 7

In an analogous manner, as described in Example 6, were prepared:
4-[3-Chloro-5-methoxy-4-[2-(piperidin-1-yl)ethyloxy]-phenyl]-thiazole-2-carboxamide hydrochloride (1:1) salt, m.p. 224°–225° C.
4-[3-Methoxy-4-[2-(piperidin-1-yl)ethyloxy]phenyl]-thiazole-2-carboxamide hydrochloride (1:1) salt, m.p. 240°–245° C.
4-[3-Chloro-5-methoxy-4-[2-(piperidin-1-yl)ethyloxy]phenyl]-N-hydroxy-thiazole-2-carboximidamide hydrochloride (1:1) salt, m.p. >260° C.
N-Hydroxy-4-[3-methoxy-4-[2-(piperidin-1-yl)ethyloxy]phenyl]-thiazole-2-carboximidamide hydrochloride (1:2) salt, m.p. >260° C.

EXAMPLE 8

4-(3-Chloro-5-methoxy-4-methylthiophenyl)-thiazole-2-carboxamide a) Ethyl 4-[3-chloro-4-[[(dimethylamino)carbonyl]thio]-5-methoxyphenyl]-thiazole-2-carboxylate (27.3 g) was added to a solution of potassium hydroxide (24.75 g) in diethylene glycol (250 ml) and stirred at 120° C. under nitrogen for 1 hr. To the cooled mixture was added iodomethane (25 ml). After stirring for 1 hr at room temperature the mixture was poured into water (1.2 l) and adjusted to pH 1 by addition of 5N hydrochloric acid. The precipitate was filtered, washed with water and dried at 40° C. under vacuum to give a solid, which was dissolved in N,N-dimethylformamide, and potassium carbonate (12 g) and iodomethane (10 ml) were added. After stirring for 1.5 hr the suspension was poured into water (800 ml). The precipitate was filtered, washed with water and dried at 50° C. under vacuum to give methyl 4-(3-chloro- 5-methoxy-4-methylthiophenyl)-thiazole-2-carboxylate (20 g).

b) In an analogous manner, as described in Example 1c, 4-(3-chloro-5-methoxy-4-methylthiophenyl)-thiazole-2-carboxamide, m.p. 201°–203° C., was prepared from methyl 4-(3-chloro-5-methoxy-4-methylthiophenyl)-thiazole-2-carboxylate.

EXAMPLE 9

4-phenyl-1H-imidazole-2-carboxamide a) A solution of ethyl aminothioxoacetate (7.4 g) in 74 ml of dichloromethane was stirred in a water bath at room temperature and treated dropwise with triethyloxonium tetrafluoroborate in dichloromethane (1.0 M, 74 ml). The mixture was stirred for 16 h and then evaporated to dryness to give a yellow oil. Anhydrous sodium acetate (9.10 g), 2-aminoacetophenone hydrochloride (9.54 g), and glacial acetic acid (110 ml) were added to the oil and the mixture was stirred and heated at 75° C. under an atmosphere of nitrogen. After 2 h the reaction mixture was evaporated and the residue was suspended in water (50 ml), slowly basified with potassium carbonate, and then extracted with ethyl acetate. The organic extracts were washed with water and brine, dried over magnesium sulphate and evaporated to dryness. The residue was crystallized from dichloromethane-diethyl ether to give 7.63 g of 4-phenyl-1H-imidazole-2-carboxylic acid ethyl ester.

b) According to the method as described in Example 1c the above-mentioned ethyl ester was converted into 4-phenyl-1H-imidazole-2-carboxamide, m.p. 210°–211° C.

EXAMPLE 10

In an analogous manner, as described in Example 9, were prepared:
4-Phenyl-1H-imidazole-2-carboxamide, m.p. 210°–211° C.
4-(3-Methylphenyl)-1H-imidazole-2-carboxamide. m.p. 270°–271° C.
4-(3,4-Dimethylphenyl)-1H-imidazole-2-carboxamide. m.p. 266°–267° C.
4-(3-Fluorophenyl)-1H-imidazole-2-carboxamide. m.p. 237°–238° C.

EXAMPLE 11

1-Methyl-4-(3-methylphenyl)1H-imidazole-2-carboxamide

A mixture of 9.79 g of 4-(3-methylphenyl)-1H-imidazole-2-carboxylic acid ethyl ester (obtained by the method of Example 9), finely ground anhydrous potassium carbonate (7.05 g), and dimethylformamide (50 ml) was stirred at room temperature for 15 min, after which iodomethane (4.0 ml) was added in one portion. After a further 30 min the reaction mixture was poured into stirred water and the precipitate was filtered off, washed with water and dried at 50° C. under vacuum to give 10.0 g of 1-methyl-4-(3-methylphenyl)-1H-imidazole-2-carboxylic acid ethyl ester, which was converted in the manner as described in Example 1c into 1-methyl-4-(3-methylphenyl)-1H-imidazole-2-carboxamide, m.p. 176°–177° C.

EXAMPLE 12

In an analogous manner as described in Example 11, were prepared:
1-Methyl-4-(3,4-dimethylphenyl)-1H-imidazole-2-carboxamide. m.p. 194°–203° C.
1-Methyl-4-(3-fluorophenyl)-1H-imidazole-2-carboxamide m.p. 149°–150° C.

EXAMPLE 13

N-Hydroxy-4-phenyl-1H-imidazole-2-carboximidamide

A suspension of 4.55 g of 4-phenyl-1H-imidazole-2-carboxamide in pyridine (30 ml) was stirred and cooled to −20° C. and treated dropwise with phosphorous oxychloride (2.3 ml) keeping the internal temperature below 0° C. After 40 min the reaction mixture was cooled to −25° C. and water (5 ml) was slowly added. The resultant suspension was poured into stirred water, carefully basified with potassium carbonate, and then filtered. The filtered solid was dissolved in dichloromethane and passed through a short column of fine silica. The column was eluted with dichloromethane-ethyl acetate (9:1), the appropriate fractions were collected and evaporated to give 4-phenyl-1H-imidazole-2-carbonitrile (2.02 g), which was treated in the manner as described in Example 3b and converted with methanesulphone acid into N-hydroxy-4-phenyl-1H-imidazole-2carboximidamide methanesulphonate (1:2), m.p. 151°–153° C.

EXAMPLE 14

In an analogous manner as described in Example 13, were prepared:
N-Hydroxy-4-(3-methylphenyl)-1H-imidazole-2-carboximidamide methanesulphonate (1:2). m.p. 143°–144° C.
N-Hydroxy-4-(3,4-dimethylphenyl)-1H-imidazole-2-carboximidamide methanesulphonate (1:2). m.p. 145°–150° C.
N-Hydroxy-4-(3-fluorophenyl)-1H-imidazole-2-carboximidamide methanesulphonate (1:2). m.p. 149°–151° C.
N-Hydroxy-1-methyl-4-(3-methylphenyl)-1H-imidazole-2-carboximidamide methanesulphonate (1:2). m.p. 163°–166° C.
N-Hydroxy-1-methyl-4-(3,4-dimethylphenyl)-1H-imidazole-2-carboximidamide methanesulphonate (1:2). m.p. 179°–185° C.
N-Hydroxy-1-methyl-4-(3-fluorophenyl)-1H-imidazole-2-carboximidamide methanesulphonate (1:2). m.p. 180°–182° C.

We claim:
1. A 4-aryl-imidazole derivative having the formula I

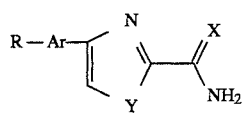

wherein
X is NOH;
Y is NH;
Ar is phenyl;
R is one to four substituents independently selected from the group consisting of hydrogen, hydroxy, lower alkyl, lower alkoxy, lower thiolalkyl, cycloalkyl, halogen, $CF_3$, $NO_2$, and O—ALK—$NR_1R_2$, in which ALK is a saturated aliphatic hydrocarbon group having from two to six carbon atoms, and $R_1$ and $R_2$ are independently hydrogen or lower alkyl, or form, together with the nitrogen atom to which they are bonded, a heterocyclic ring consisting of a 5- or 6-membered ring and wherein said heterocyclic ring may contain a second hereto atom of nitrogen or oxygen and be substituted with a lower alkyl; or a pharmaceutically salt thereof.

2. The derivative of claim 1, wherein at least one of the substituents R is methyl, methoxy or chlorine.

3. A 4-aryl-imidazole derivative comprising N-hydroxy-4-(3,4-dimethylphenyl) 1H-imidazole-2-carboximidamide or pharmaceutically acceptable salts thereof.

4. A method of treating heart failure in mammals comprising administering pharmaceutically effective amounts of a 4-aryl-imidazole derivative having the formula I

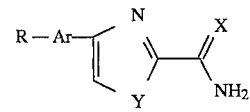

wherein
X is O or NOH;
Y is $NR_3$;
Ar is a group selected from the group consisting of phenyl, naphthyl, tetrahydronaphthyl, and biphenyl;
R is one to four substituents independently selected from the group consisting of hydrogen, hydroxy, lower alkyl, lower alkoxy, lower thioalkyl, cycloalkyl, halogen, $CF_3$, $NO_2$, and O—ALK—$NR_1R_2$, in which ALK is a saturated aliphatic hydrocarbon group having from 2 through 6 carbon atoms, and $R_1$ and $R_2$ are independently hydrogen or lower alkyl, or form, together with the nitrogen atom to which they are bonded, a heterocyclic ring consisting of a 5- or 6-membered ring and wherein said heterocyclic ring may contain a second hetero atom of nitrogen or oxygen and be substituted with lower alkyl; and $R_3$ is hydrogen or a lower alkyl; or a pharmaceutically acceptable salt thereof, to mammals experiencing heart failure.

5. A method of treating asthma in mammals comprising administering pharmaceutically effective amounts of a derivative having the formula I

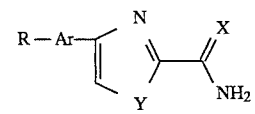

wherein
X is O or NOH;
Y is $NR_3$;
Ar is a group selected from the group consisting of phenyl, naphthyl, tetrahydronaphthyl, and biphenyl;
R is one to four substituents independently selected from the group consisting of hydrogen, hydroxy, lower alkyl, lower alkoxy, lower thioalkyl, cycloalkyl, halogen, $CF_3$, $NO_2$, and O—ALK—$NR_1R_2$, in which ALK is a saturated aliphatic hydrocarbon group having from 2 through 6 carbon atoms, and $R_1$ and $R_2$ are independently hydrogen or lower alkyl, Or form, together with the nitrogen atom to which they are bonded, a heterocyclic ring consisting of a 5- or 6-membered ring and wherein said heterocyclic ring may contain a second hetero atom of nitrogen or oxygen and be substituted with lower alkyl; and R₃ is hydrogen or a lower alkyl; or a pharmaceutically acceptable salt thereof, to mammals with asthma.

* * * * *

UNITED STATES PATENT AND TRADEMARK OFFICE
CERTIFICATE OF CORRECTION

PATENT NO. : 5,462,959
DATED : October 31, 1995
INVENTOR(S) : Pick et al.

It is certified that error appears in the above-indentified patent and that said Letters Patent is hereby corrected as shown below:

Please correct the claims as follows:

Claim 1, column 10, line 5, delete "hereto" and replace with -- hetero --;
line 8, after "pharmaceutically", please insert -- acceptable --.

Claim 3, column 10, lin 12, after "4-(3,4-dimethylphenyl)", please insert -- - --.

Claim 5, column 10, line 65, delete "Or" and replace with -- or --.

Signed and Sealed this

Sixteenth Day of July, 1996

Attest:

BRUCE LEHMAN

Attesting Officer          Commissioner of Patents and Trademarks